United States Patent [19]

Tatsuno et al.

[11] Patent Number: 5,282,967
[45] Date of Patent: Feb. 1, 1994

[54] METHOD FOR FEEDING GERM-FREE PURE WATER

[75] Inventors: Toshio Tatsuno; Mitsuo Miyamoto, both of Osaka; Yoshiharu Ohta; Koichi Sawada, both of Tokyo, all of Japan

[73] Assignees: Morita Kagaku Kogyo Co., Ltd.; Normura Micro Science Co., Ltd., both of Japan

[21] Appl. No.: 888,429

[22] Filed: May 28, 1992

Related U.S. Application Data

[63] Continuation of Ser. No. 487,934, Mar. 5, 1990, abandoned.

[30] Foreign Application Priority Data

Mar. 6, 1989 [JP] Japan .................... 1-52154
Apr. 27, 1989 [JP] Japan .................... 1-105885

[51] Int. Cl.$^5$ .......................................... B01D 61/58
[52] U.S. Cl. .................................. 210/638; 210/641; 210/651; 210/652
[58] Field of Search .............. 422/37, 28; 210/257.2, 210/259, 266, 641, 651, 652, 650, 639, 638

[56] References Cited

U.S. PATENT DOCUMENTS

| | | | |
|---|---|---|---|
| 3,887,482 | 6/1975 | Hellestam et al. | 210/753 |
| 4,436,645 | 3/1984 | Ceaser | 210/753 |
| 4,795,497 | 1/1989 | McConnell et al. | 134/99 |
| 4,936,955 | 6/1990 | Dobson et al. | 202/154 |
| 5,147,605 | 9/1992 | Tatsuno et al. | 422/37 |

FOREIGN PATENT DOCUMENTS

| | | | |
|---|---|---|---|
| 0217198 | 1/1985 | Fed. Rep. of Germany | 210/753 |
| 3431101 | 3/1986 | Fed. Rep. of Germany | 210/753 |
| 1584845 | 3/1977 | United Kingdom . | |

OTHER PUBLICATIONS

Block; *Disinfection, Sterilization, and Preservation*, 1983, p. 682.

*Primary Examiner*—Frank Spear
*Attorney, Agent, or Firm*—Larson and Taylor

[57] ABSTRACT

A method of feeding pure water under germ-free conditions is provided by purifying raw water into primary water by successive passage through a defined series of purification units, temporarily storing the primary water in a primary water tank, further purifying the stored water to still higher purity by passage through a defined series of purification units; injecting HF or a salt of HF into the thus-purified water in bacteriostatic and sterilizing concentrations and then feeding it to its point of use.

6 Claims, 8 Drawing Sheets

METHOD FOR FEEDING GERM-FREE PURE WATER

This application is a continuation of application Ser. No. 07/487,934 filed Mar. 5, 1990, now abandoned.

SUMMARY OF THE INVENTION

The present invention relates to a method for feeding pure water steadily or continually under germ-free conditions for use in technical fields, for example in the electronics, chemical, medicinal, manufacture of highly precise-shaped parts, and foodstuff industries, where a water of high purity and free of any microbial cells, namely germ-free pure water, is needed.

BACKGROUND OF THE INVENTION

There is an ever-increasing demand in recent years for water of high-purity to be used in the production processes or washing steps which are effected in the industries of electronics, chemicals, manufacture of precise-shaped parts and industry of foods. Moreover, such high-purity water is always required to be germ-free pure water. In the pure water-producing and feeding systems or plants employed in these industrial fields, pure water as produced by such systems is used for various purposes. In the industry of chemicals, for example, there is a tendency that the systems for production of pure water to be used in the dissolution of raw materials, washing, formulation of preparations and dilution would be bigger and more complex. This tendency is enhanced further when the existing systems are modified or extended.

Many tanks, valves, pumps, filters and lengthy pipes are used and arranged in the pure water-producing and feeding systems causing the systems to become larger and more complex as described above, so that an environment is provided where viable cells of, microorganisms can more readily grow and develop. Further, a pure water feed line of the pure water-producing system is provided with many branch pipings. Accordingly, the pure water feed line tends to have spots or places where pure water stagnates and does not flow smoothly, in other words, water-stagnant pockets, so that the viable cells are likely to grow therein. When the system is in operation, pure water does not flow but rather remains stagnant throughout the system, further promoting the growth of viable cells. To minimize this problem, some plants have arranged a recirculation line for returning pure water to a pure water-containing tank which is incorporated into the pure water-producing system so that pure water is steadily circulated through the system to eliminate any water-stagnant spots, thereby preventing the growth of the viable cells. In another instances, each point of use i.e. wherever it is used of pure water is arranged to be equipped with a refiltration unit.

In addition, the pure water feed line must be subjected to periodical sterilization to kill the viable cells. A conventional sterilization procedure is to treat pure water for 1 hour with an aqueous solution of 1–3 wt. % hydrogen peroxide or with an aqueous solution of 1–5 ppm of sodium hypochlorite. These conventional methods are however accompanied by the problems that a great volume of waste water effluent which requires further treatment thereof if discharged after the sterilization process and use of a strong oxidizing agent such as hydrogen peroxide or sodium hypochlorite may oxidize and decompose ion-exchange resins, membrane filters and the like as arranged in the pure water-producing system. The conventional methods are also accompanied by the drawback that the system must be washed with a great deal of pure water to discharge the microcidal agent after the completion of the sterilization process.

Other sterilization methods include steam sterilization and hot-water sterilization. These methods are not considered to be very economical when their energy efficiency is taken into consideration.

For the reasons mentioned above, a great deal of energy, cost, labor and operation time are still indispensable for the continual or constant feeding of germ-free pure water from an enlarged and complicated pure water-producing and feeding system which continues to become greater and more complex.

An object of the present invention is therefore to solve many of the above-mentioned problems which the conventional methods encounter upon sterilization of the system for producing and feeding a water of high-purity, and to provide such a method which is easy to practice and can continually feed the germ-free pure water even in an enlarged and complicated system.

DETAILED DESCRIPTION OF THE INVENTION

The present inventors have proceeded with a variety of investigations with a view toward achieving the above object.

Certain fluorine compounds have been used as dental follicle decay preventives and wood preservatives for many years and have been known to exhibit specific biological activities against organisms. With this knowledge, the present inventors have conducted tests in an attempt to control or combat such living cells of microorganisms which are capable of growing in pure water, for example, pseudomonades, fungi and the like, and thus have conducted a detailed investigation on the influence of various water-soluble compounds, which are intentionally incorporated into pure water, against the growth of such microorganisms, with changing concentrations of such compounds. As a result, we have now found that the incorporation of fluoride ions even at a trace level in a pure water can bring about surprisingly high sterilization effects against microbial cells. Namely, we have now found that the maintenance of fluoride ions as incorporated even at a level as low as 10 ppm or even lower in a pure water can completely kill or combat viable cells; and such a bacteriostatic state that viable cells in the water are not allowed to multiply can be attained even at still lower fluoride ion levels of 1 ppm and below. Although the sterilization mechanism which is exerted by such an extremely small level of fluoride ions has not been fully elucidated, it appears that the fluoride anions exhibit certain unique physiological or biological activities which are distinguishable from the sterilization effects of the conventional sterilization processes which are dependent on the effects of a specific hydrogen ion concentration (pH) or the effects of the reactions of oxidation/reduction.

It has also been recognized that the fluoride ion concentration which is effective for the prevention of growth of viable cells in pure water may vary depending on the nature of the compound employed to supply the fluoride anions hydrofluoric acid (HF) is effective at concentrations of 0.1 ppm and higher, preferably 0.1–100 ppm and a water-soluble fluoride salt, for example, an alkali metal fluoride or ammonium fluoride is effective at concentrations of 1 ppm and higher, preferably 1-100 ppm. Concentrations substantially higher than 100 ppm can certainly bring about the desired sterilization effects but the resultant solution in pure water may not be taken and used as a pure water in some instances. In addition, such excessive concentrations of HF or the metal fluoride require substantial labor and time for the complete elimination of the fluoride compound, if this elimination of the fluoride will be required upon later use of the germ-free pure water as fed.

In a first aspect of the present invention, there is thus provided a method for feeding germ-free pure water through a pure water feed line, which comprises providing the presence of hydrofluoric acid at a concentration of 0.1-100 ppm in pure water to be fed, said pure water being contained in the pure water feed line, whereby the pure water is fed while being maintained under germ-free conditions with the growth of viable cells of microorganisms being suppressed by the fluoride ions present in the pure water.

In a second of the present invention, there is also provided a method for feeding germ-free pure water through a pure water feed line, which comprises providing the presence of a water-soluble fluoride salt at a concentration of 1-100 ppm in a pure water to be fed, said pure water being contained in the pure water feed line, whereby the pure water is fed while being maintained under germ-free conditions with the growth of viable cells of microorganisms being suppressed by the fluoride ions present in the pure water.

In accordance with the present methods of this invention, providing the presence of hydrofluoric acid or the fluoride salt in pure water may be achieved by incorporation of hydrofluoric acid or the fluoride salt as its aqueous solution in pure water.

The germ-free pure water as fed by either one of the above methods of the first and second aspects of the present invention is directly usable as such for such applications that permit the presence of the fluoride compound as incorporated at a trace level in pure water. If desired, the fluoride compound can be completely eliminated before use of the pure water, for example by treatment with an ion-exchange resin. In the present invention, hydrofluoric acid or a fluoride salt is intermittently or continuously incorporated in the form of an aqueous solution into a pure water to be sterilized and is thus caused to exist at the required concentration of 0.1-100 ppm or 1-100 ppm., in the pure water. The sterilizing agent can be added at any desired locations along a pure water feed line comprised of pure water-producing and feeding system, especially at a point in a pure water feed piping. The term "water-soluble" for the water-soluble fluoride salt means that the fluoride salt has such solubility that it can be dissolved at a concentration of 1-100 ppm in water. Suitable examples of the fluoride salt available in the present invention include the fluorides of alkali metals, for example, sodium fluoride, potassium fluoride and lithium fluoride; the fluorides of alkaline earth metals, for example, calcium fluoride and magnesium fluoride; ammonium fluoride; the fluorides of iron and other appropriate metals; etc.

A test was conducted to investigate the sterilization effects and microcidal or bacteriostatic effects of various compounds which were employed at extremely low concentrations of 1-100 ppm. The various compounds under test were separately added to portions of a 1,000-fold diluted aqueous solution of an ordinary liquid agar culture medium so as to prepare different test solutions containing the test compounds at predetermined different concentrations, respectively. Viable cells of microbial species which had been separated from an existing pure water, namely, which had been isolated by passing through a microporous membrane a volume of pure water as sampled out from an existing pure water-producing system, were inoculated in a suitable amount (initial inoculum size of viable cells: $5 \times 10^4$ cells/ml) to each test solution as prepared. After test solution containing the cells was incubated under stationary conditions at 30° C. for 4 days, the number of viable cells so incubated was counted by the known MF method (i.e., the viable cell count was determined in accordance with the procedure of JIS K0101).

The viable cell counts thus determined are summarized in Table 1.

TABLE 1

| Kind and amount of test compound added to test solution | | Viable cell counts (cells/ml) | Sterilization effects |
|---|---|---|---|
| Not added | | $5 \times 10^5$ | — |
| HF | 1 ppm | $3 \times 10^3$ | ± |
| HF | 10 ppm | 0 | + |
| HF | 100 ppm | 0 | + |
| $NH_4F$ | 50 ppm | $5 \times 10^3$ | ± |
| $NH_4F$ | 100 ppm | 3 | + |
| NaF | 50 ppm | $3 \times 10^2$ | ± |
| NaF | 100 ppm | 50 | + |
| $H_2O_2$ | 10 ppm | $5 \times 10^5$ | — |
| $H_2O_2$ | 1000 ppm | $1 \times 10^2$ | ± |
| HCl | 10 ppm | $3 \times 10^3$ | ± |
| HCl | 1000 ppm | $3 \times 10^3$ | ± |
| NaCl | 100 ppm | $5 \times 10^5$ | — |

(Initial viable cell count: $5 \times 10^4$ cells/ml)

In Table 1, such concentrations of the test compound at which the sterilizing effects were observed are indicated by +, those concentration indicative of growth of the microbial cells is shown by —, and those concentration indicative of the bacteriostatic effects is shown by ±. From the test results, the sterilization effects by HF are clearly envisaged. It should be noted that no sterilization effects are observed from the addition of HCl at the concentration of 10 ppm. It is thus understood that the sterilization action of HF is not simply due to a change in pH-values but is inherent to the fluoride anions. It is also understood that the fluoride salts under test can exhibit the sterilization effects at certain concentrations. No sterilization effects were observed even when NaCl was added at the concentration of 100 ppm., similarly to HCl. The sterilization effects of the fluoride salts should therefore be attributable to the fluoride anions yielded therefrom.

Table 1 shows the sterilization or bacteriostatic action of hydrofluoric acid at 100 ppm and the water-soluble fluoride salts at 50 ppm or 100 ppm. Since the behavior of viable cells was investigated with incubating in the 1000-fold diluted solution of the ordinary liquid agar medium in the present tests, it is possible to say that the sterilization and/or bacteriostatic action as tested in the above was investigated in an environment in which viable cells can grow very easily. Because pure water is substantially free of such substances which may serve as nutrient sources for viable cells, hydrofluoric acid and water-soluble fluoride salts can exhibit sufficient sterilization and bacteriostatic effects in the pure water even when they are present at still lower concentrations in pure water. The present inventors have found that hydrofluoric acid is sterilizingly effective at 0.1–100 ppm while water-soluble fluoride salts are effective at 1–100 ppm.

The present invention will hereinafter be described specifically with reference to FIG. 1 of the accompanying drawings, which illustrates an exemplary, pure water-producing and feeding system or plant suitable for use in the practice of the method of the present invention.

Figure 1:
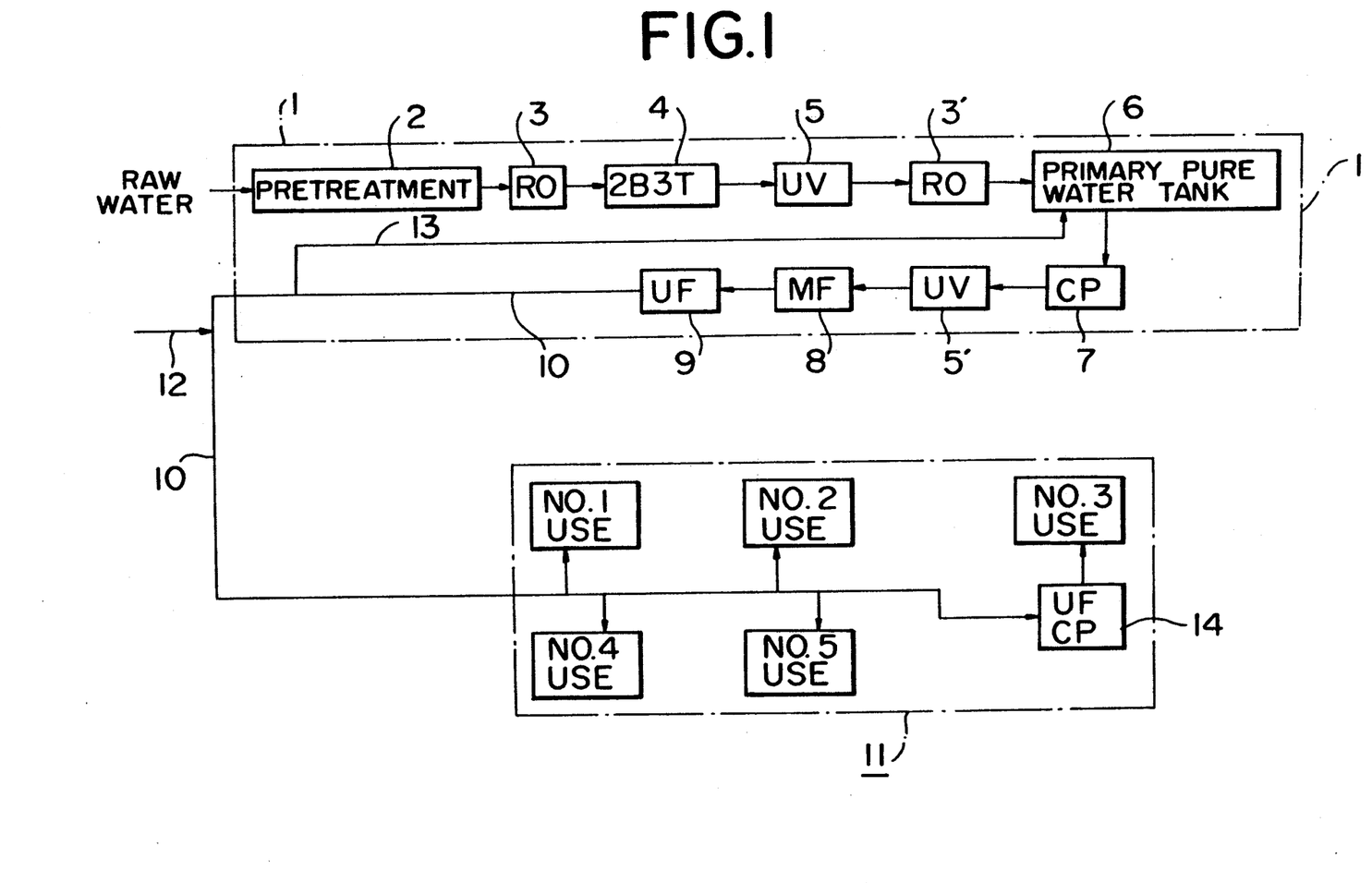
FIG. 1 shows a simplified flow diagram of a pure water-producing and feeding system having a pure water feed line which is suitable for use in the practice of each method of the present invention.

FIG. 1 is a simplified flow diagram of the pure water-producing and feeding system which is provided with a pure water feed line. As illustrated in FIG. 1 of the drawings, raw water is purified into primary pure water through a pretreatment unit 2, a reverse osmosis membrane unit 3, ion-exchange unit 4 of 2-bed/3-column-type, an ultraviolet-radiating sterilizer unit 5 and a reverse osmosis membrane unit 3', which are successively installed in the pure water-producing system 1. The primary pure water is temporarily stored in a primary water tank 6. To convert the primary pure water into pure water of still higher purity, the primary pure water is then passed and processed through a cartridge-type polisher (namely, an ion-exchange resin unit) 7, an ultraviolet-radiating sterilizer unit 5', a membrane-type filter 8 and an ultrafiltration unit 9, whereby the desired high-purity water is obtained eventually. The high-purity water is thereafter distributed to individual use points 11 for use of pure water by being fed through a pure water feed line 10. A certain portion of the high-purity water is branched out from a suitable point on the pure water feed line 10 and is returned to the pure water tank 6 by way of a return line 13.

According to the first aspect of the present invention, an aqueous solution of hydrofluoric acid is either intermittently or continuously injected through its feed tube 12 connected to the pure water feed line 10 at a suitable point, for example, by means of a chemical feeder pump at such a rate that the concentration of fluoride ions in the pure water flowing in the piping arranged immediately downstream of the pure water-producing system 1, namely, in the pure water feed line positioned downstream of said suitable point will be amounting to 0.1–100 ppm. The aqueous solution of hydrofluoric acid is thus uniformly mixed with the pure water to provide the presence of fluoride ions in the pure water. The amount of fluoride ions to be incorporated into and present in the pure water may be adjusted by such parameters as the nature and the cell number of microbial species developed and grown in the system, temperature and residence time of water in the system. Fluoride ion concentrations of higher than 100 ppm may however bring about certain adverse effects such as corrosion to the materials of the equipments. On the other hand, fluoride ion concentrations of lower than 0.1 ppm cannot exhibit the sterilization effects fully.

According to the second aspect of the present invention, in place of hydrofluoric acid, an aqueous solution of a salt of hydrofluoric acid (i.e., the fluoride salt), e.g., $NH_4F$, $NaF$ or $KF$ is injected to give a fluoride salt concentration of 1–100 ppm in the pure water.

Pure water containing the fluoride anions thus incorporated is used as such at individual use points for use of pure water, so long as the presence of fluoride ions in the trace amount does not cause any objectionable problem. If the presence of fluoride ions is objectionable in view of the application purpose of pure water, it may be necessary to arrange a polisher 14 containing an ion-exchange resin, before the use point of Use No. 3 as shown in FIG. 1, for instance, so that the sterilized pure water is caused to flow through the polisher 14 to effect the elimination of fluoride ions before the pure water is actually used. The aqueous solution of hydrofluoric acid or a salt thereof is injected directly into the pure water flowing in the water-delivery piping of the pure water-producing system in the illustrated embodiment. A tank may be however be inserted in the line 10 in order to temporarily store pure water in said tank before the pure water is supplied to the individual points of use of pure water by a pump or any other suitable forced feeding means. If appropriate, the aqueous solution of hydrofluoric acid or a salt thereof may also be injected into the pure water which is being stored in said tank.

The present invention can bring about the necessary sterilization effects and bacteriostatic effects in pure water by simply incorporating a trace amount of fluoride ions into the water so that they exist in pure water. For example, the incorporation of the fluoride ions may simply be effected using a chemical feed pump arranged at an intermediary point of a pure water-producing and feeding system. The present invention has therefore made it possible to feed pure water continually under germ-free conditions even in an enlarged and complicated system.

With reference to the accompanying Drawings.

The present invention will hereinafter be described based on the following Examples and Comparative Example.

EXAMPLE 1

A pure water-producing and feeding system having the pure water feed line shown in FIG. 1 and capable of feeding pure water at a rate of 4 $m^3$ per hour was operated under the following conditions.

(a) Initial Sterilization with $H_2O_2$ by Conventional Method

An aqueous 35% $H_2O_2$ solution was added to primary pure water so that an aqueous 1% $H_2O_2$ solution in primary pure water was formed and stored in the primary pure water tank 6.

Conduits as connected to the inlet and outlet of the cartridge-type polisher (ion-exchange resin unit) 7 were disconnected from the polisher 7 and were connected directly to each other, whereby there was formed a connected bypass circuit which extends outside the polisher 7. Thereafter the 1% $H_2O_2$ solution as stored was fed from the tank 6 via the units 5', 8 and 9 into the pure water feed line 10 leading to the use point 11 and was returned in part back into the tank 6 via the return line 13. During this, the 1% $H_2O_2$ solution was drained at the respective use points No. 1, No. 2, No. 4 and No. 5 which are arranged in the whole use point 11 and at which pure water is actually consumed. After the system was thus operated to run for 1 hour, the $H_2O_2$ solution was allowed to remain for 1 hour in the respective units of the system and the lines to expose their inner walls to the $H_2O_2$ solution. Each unit and line were thereafter flushed and washed with pure water to expell out the $H_2O_2$ solution therefrom. At Use Point No. 1, it was confirmed that the electric resistivity and cell count of the water withdrawn therefrom were 17.5 $M\Omega.cm$ and zero cell/100 ml, respectively.

(b) Frequency of Measurement and Method for Measurement of Cell Count

The commercial production and feeding of pure water were re-started. Sampling of pure water was conducted once every five days of operation of the system by drawing a pure water sample at Use point No. 1. With respect to each pure water sample, the number of viable cells per 100 ml of pure water sample was counted by the known viable cell counting method (the method of JIS K0101) which makes use of the membrane filter technique.

(c) Operation of the Pure Water-Producing System with Practicing the Method of the Present Invention After the above-described initial sterilization with $H_2O_2$ was conducted, commercial production of germ-free pure water was commenced by feeding primary pure water at a flow rate of 4 $m^3/hr$ into the primary water tank 6.

At the same time, primary pure water was pumped at flow rate of 8 $m^3/hr$ from the primary pure water tank 6. The primary pure water from the tank 6 was pumped to flow through the cartridge-type polisher (cartridge-type mixed-bed ion-exchange resin unit) 7, ultraviolet sterilizer unit 5', membrane filter 8 and ultrafiltration unit 9 successively, wherein the primary pure water was thereby purified into pure water of high-purity. Of the high-purity pure water as produced, about 4 $m^3/hr$ stream of the high-purity pure water was branched and returned via the return line 13 to the primary pure water tank 6 so that about 4 $m^3/hr$ stream of the high-purity pure water was sent through the pure water feed line 10 to the use point 11.

In the present Example, an aqueous solution of hydrofluoric acid was injected into the high-purity pure water in the line 10 by a chemical feeder pump (not shown) through the feed tube 12 at a point downstream of the place of connection between the pure water feed line 10 and the return line 13 to the primary pure water tank 6. HF was incorporated in such an amount that the concentration of fluoride ions in the high-purity pure water became 1 ppm.

Figure 2:
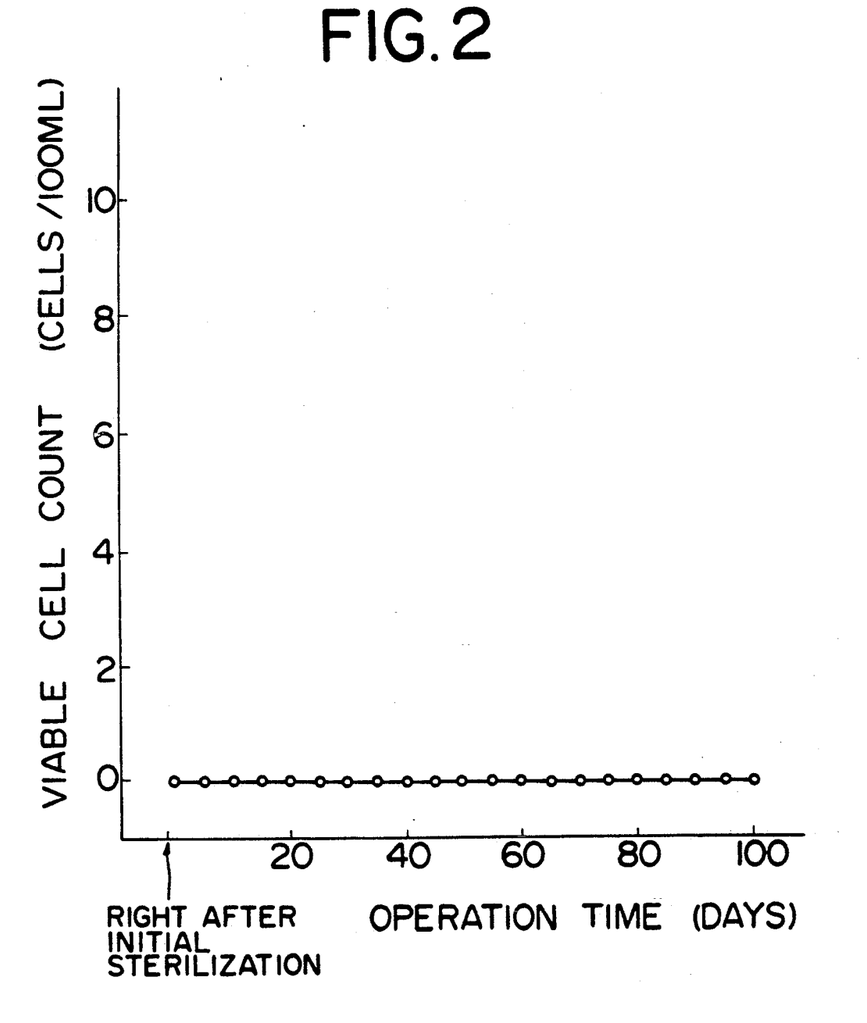
FIGS. 2, 4–7 and 8 show graphs of the curves illustrating time-dependent variations of the viable cell counts which were measured in the germ-free pure water samples obtained in the Examples 1, 3–6 and 7 of this invention respectively.

Following the initial sterilization with $H_2O_2$ described above, said commercial production and feeding of high-purity pure water with incorporation of HF were continued in the above described manner. At the same time, the replenishment of fluoride ions was also continued. A pure water sample was drawn on every fifth day of operation of the system at Use Point No. 1 and the number of viable cells in the water sample was counted in the manner described above. Time-dependent variation in the viable cell count as measured was plotted as a curve shown in FIG. 2 of the accompanying drawings. It was possible to feed germ-free pure water continually for at least 90 days as measured at Use Point No. 1.

COMPARATIVE EXAMPLE 1

The initial sterilization with $H_2O_2$ and the commercial production and feeding of pure water were conducted in the same manner as in Example 1 except that the injection of aqueous HF was omitted.

Figure 3:
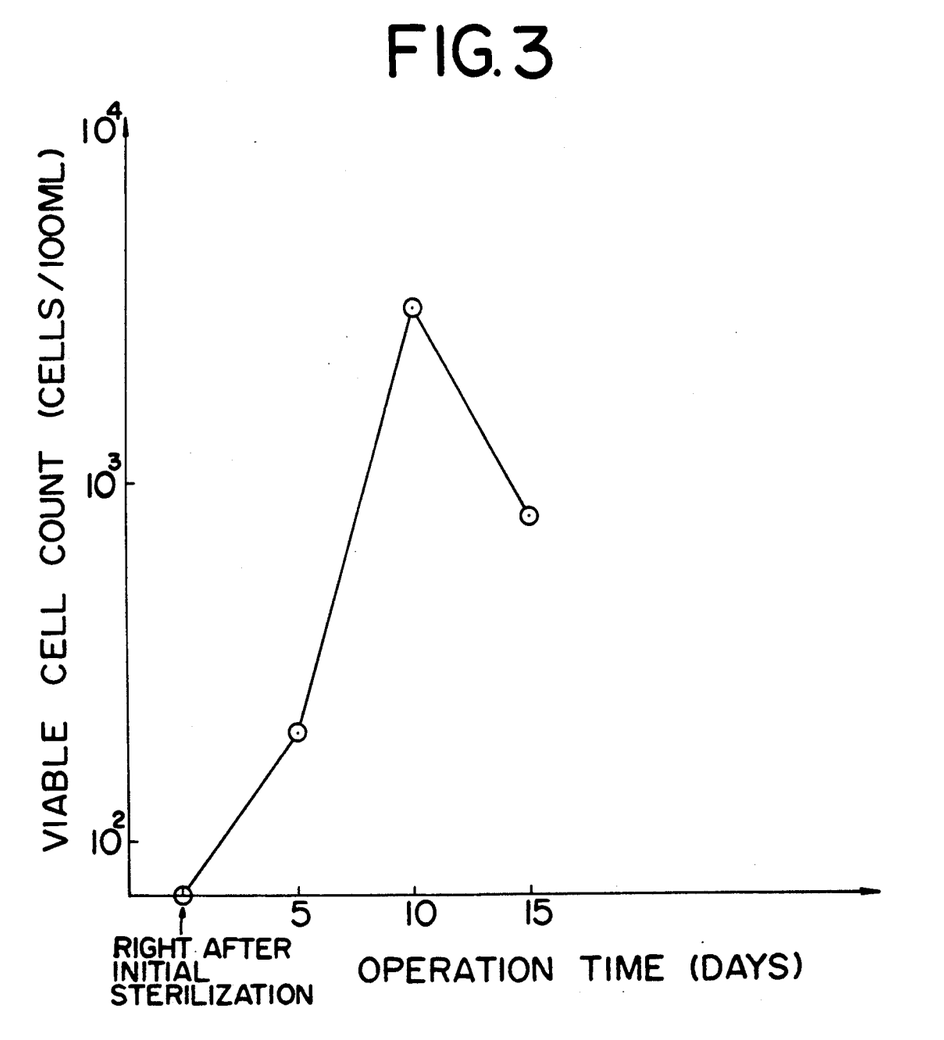
FIG. 3 shows a graph of a curve illustrating, in semi-logarithm way, time-dependent variations of the viable cell count which was measured in pure feed water obtained in Comparative Example 1 where the present invention was not practiced.

With respect to the respective pure water samples withdrawn at Use Point No. 1, the numer of viable cells was counted as in Example 1. Time-dependent variation in the viable cell count as measured was plotted in semlogarithm way as a curve shown in FIG. 3 of the accomanying drawing. Viable cells were discovered already on the fifth day of operation of the system after the initial sterilization with $H_2O_2$ and continued to increase greatly thereafter.

EXAMPLE 2

After the initial sterilization with $H_2O_2$ was conducted in the same manner as in Example 1, the procedure of Example 1 was repeated while an aqueous solution of hydrofluoric acid was replenished as in Example 1 so that the concentration of hydrofluoric acid in the pure water in the feed line 10 was maintained at 100 ppm.

It was possible to feed germ-free pure water continually for at least 90 days of operation of the system at Use Point No. 1.

EXAMPLE 3

The procedure of Example 1 was repeated except that an aqueous solution of ammonium fluoride was injected to give an ammonium fluoride concentration of 50 ppm to the pure water in the feed line 10.

Figure 4:
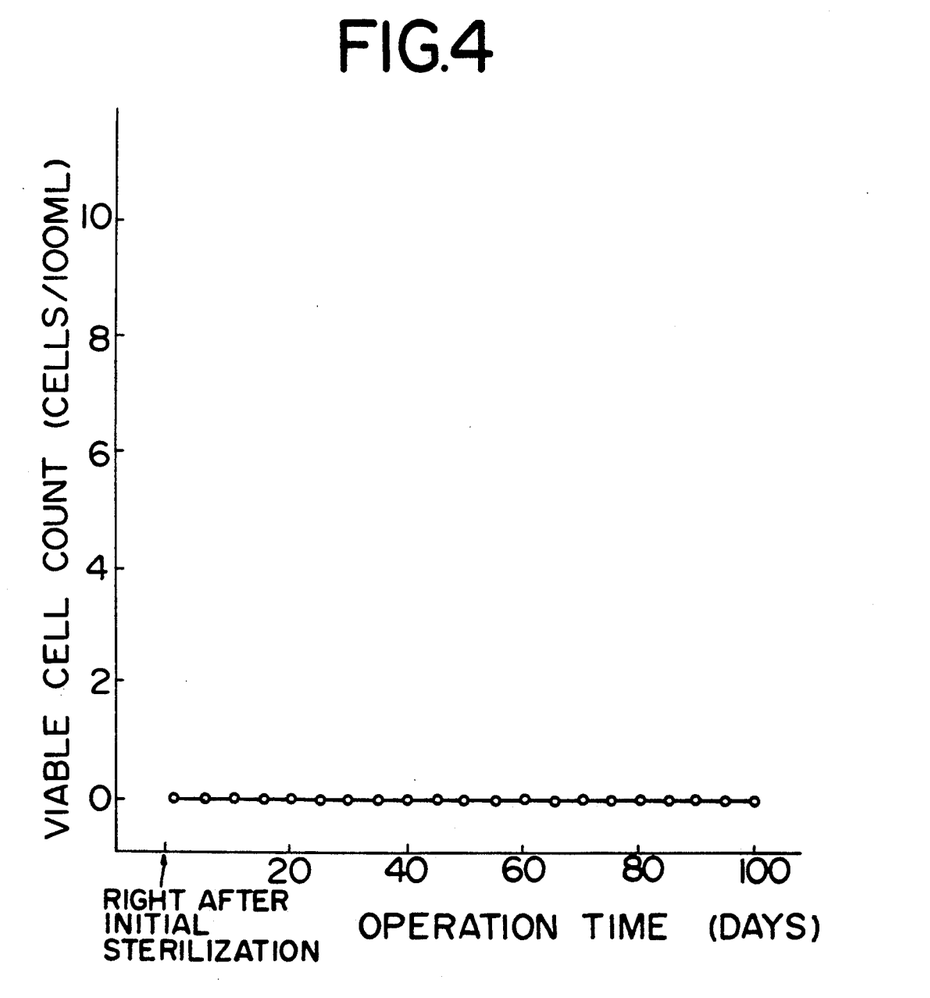

Measurement results of viable cell count in pure water samples withdrawn at Use Point No. 1 are shown in FIG. 4. It was possible to feed germ-free pure water continually for at least 90 days of operation of the system after the initial sterilization with $H_2O_2$.

EXAMPLE 4

The procedure of Example 1 was repeated except that an aqueous NaF solution was injected to give an NaF concentration of 50 ppm to the pure water in the feed line 10.

Figure 5:
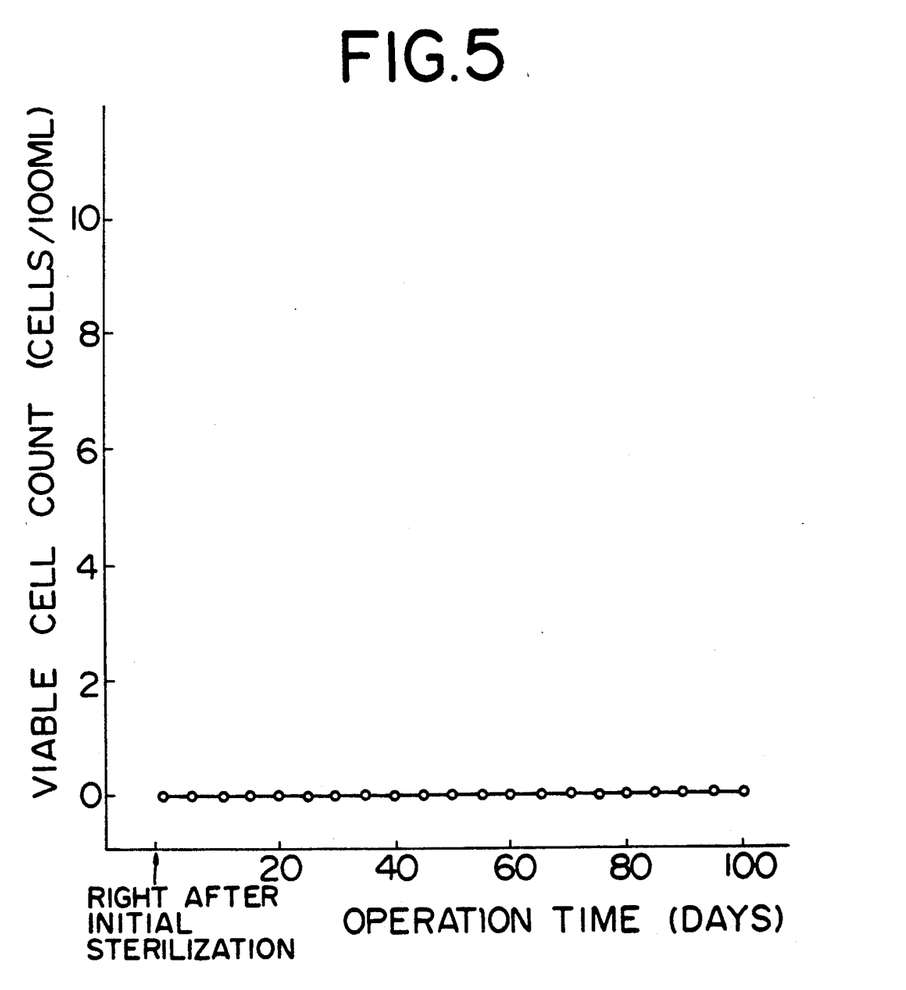

Measurement results of viable cell count in pure water samples drawn at Use Point No. 1 are depicted in FIG. 5. It was possible to feed germ-free pure water continually for at least 90 days.

EXAMPLE 5

The procedure of Example 1 was repeated except that an aqueous solution of hydrofluoric acid was injected to give an HF concentration of 0.1 ppm to the pure water in the feed line 10.

Figure 6:
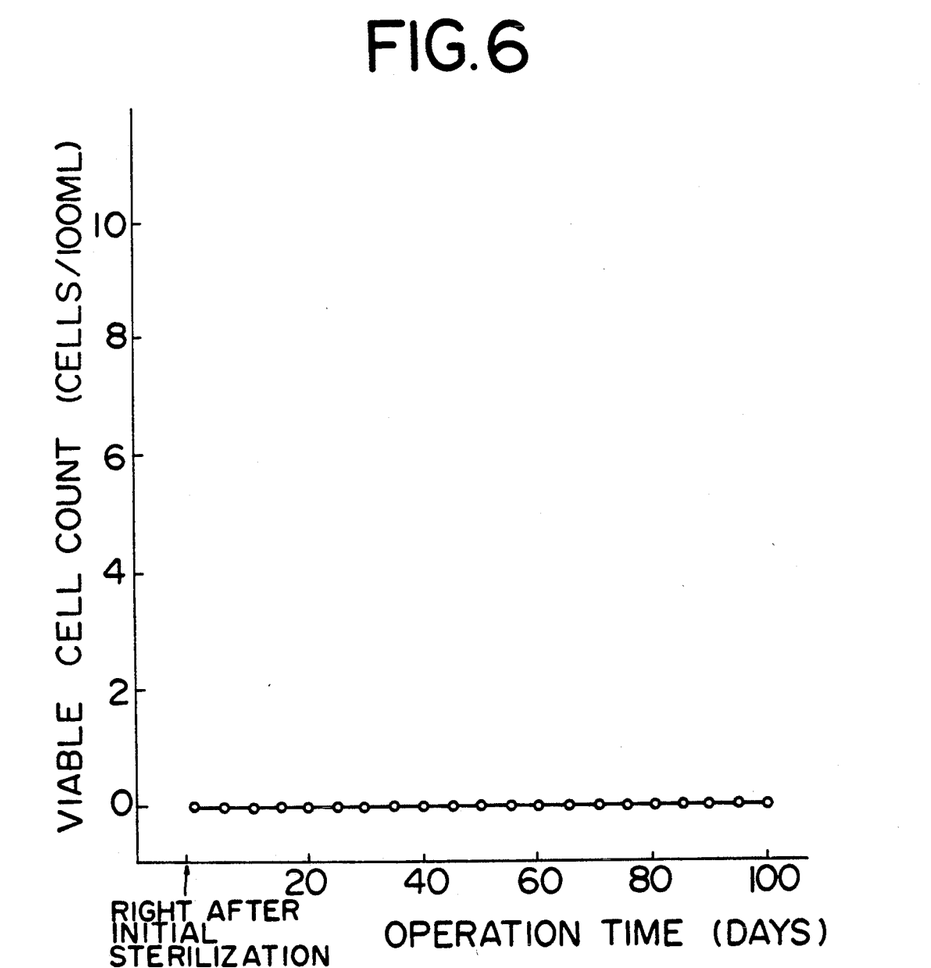

Measurement results of viable cell count in pure water samples drawn at Use Point No. 1 are plotted in FIG. 6. It was possible to feed germ-free pure water continually for at least 90 days after the initial sterilization with $H_2O_2$.

EXAMPLE 6

The procedure of Example 1 was repeated except that an aqueous solution of ammonium fluoride was injected to give an $NH_4F$ concentration of 1 ppm to the pure water in the feed line 10.

Figure 7:
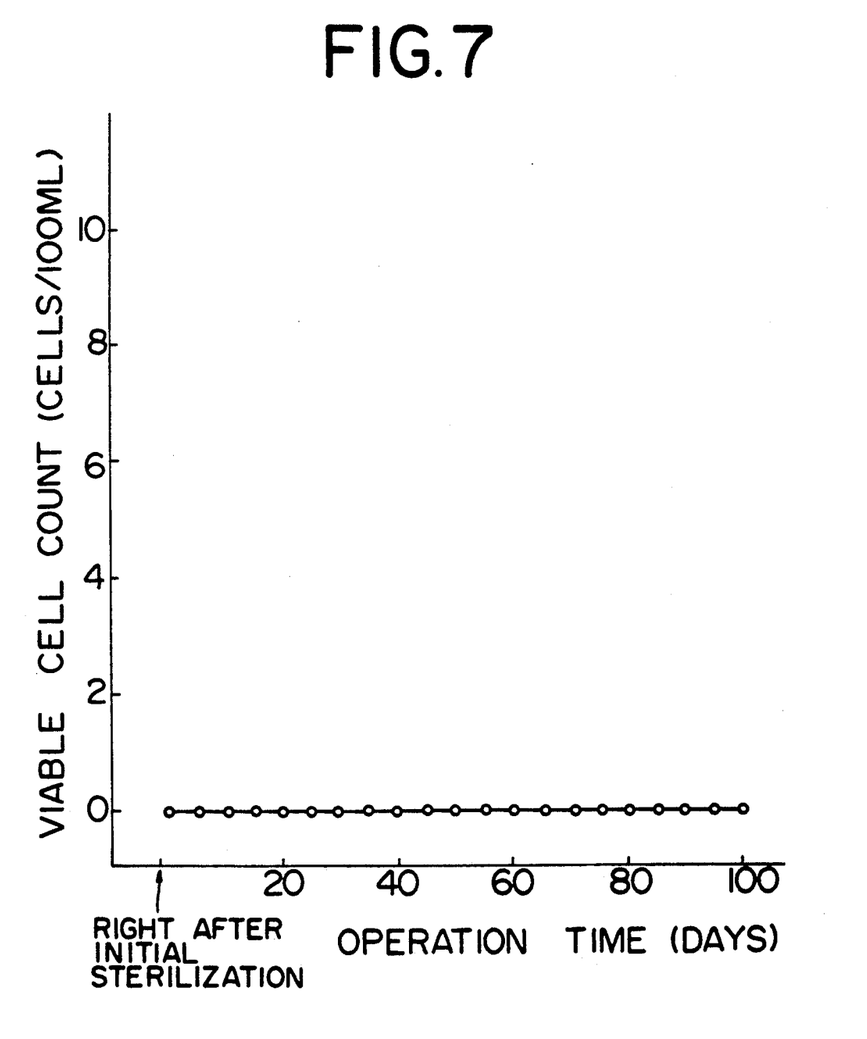

Measurement results of viable cell count in pure water samples drawn at Use Point No. 1 are plotted in FIG. 7. It was possible to feed germ-free pure water continually for at least 90 days after the initial sterilization.

EXAMPLE 7

The procedure of Example 1 was repeated except that an aqueous NaF solution was added to give an NaF concentration of 1 ppm to the pure water in the feed line 10.

Figure 8:
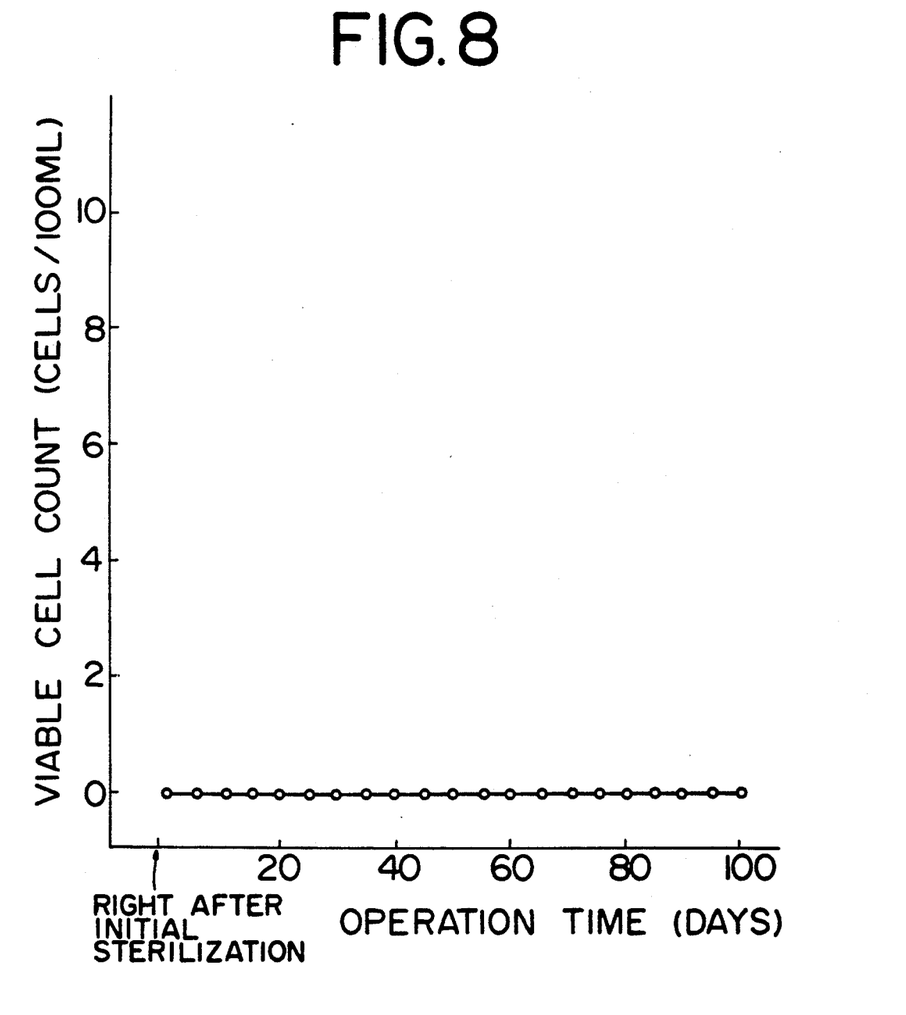

Measurement results of viable cell count in pure water samples drawn at Use Point No. 1 are plotted in FIG. 8. It was possible to feed germ-free pure water continually for at least 90 days.

We claim:

1. A method for feeding germ-free pure water having a purity higher than that of primary pure water and lower than that of ultrapure water but containing a trace of hydrofluoric acid, which comprises feeding a primary pure water than has been obtained by purification of raw water by successive passages through a pretreatment unit, a reverse osmosis membrane unit, an ion-exchange unit, an ultraviolet-irradiating sterilizer unit and a reverse osmosis membrane unit, to a tank for a storage of the primary pure water, withdrawing the primary pure water from said tank, further purifying the primary pure water by passing it through an ion-exchange resin unit in the form of a cartridge-type polisher, an ultraviolet-irradiating sterilizer unit, a membrane-type filter and an ultrafiltration unit to obtain pure water having a purity higher than that of the primary pure water but lower than that of ultrapure water, passing the resulting pure water into and through a pure water feed line as connected to said ultrafiltration unit and leading to individual use point(s) of pure water, incorporating a trace amount of hydrofluoric acid alone into the flow of the pure water within the pure water feed line at one or more locations of the pure water line to provide a presence of hydrofluoric acid at a bacteriostatic and sterilizing concentration of 0.1 to 10 ppm. in the flow of the pure water and thereby enabling the pure water to be maintained under germ-free conditions during its passage through the pure water feed line, and feeding the resulting germ-free pure water containing the trace of hydrofluoric acid out of the pure water feed line at the use point(s) of pure water.

2. A method for feeding germ-free pure water having a purity higher than that of primary pure water and lower than that of ultrapure water but containing a trace of a water-soluble fluoride salt, which comprises feeding a primary pure water that has ben obtained by purification of raw water by successive passages through a pretreatment unit, a reverse osmosis membrane unit, an ion-exchange unit, an ultraviolet-irradiating sterilizer unit and a reverse osmosis membrane unit, to a tank for storage of the primary pure water, withdrawing the primary pure water from said tank, further purifying the primary pure water by passing it through an ion-exchange resin unit in the form of a cartridge-type polisher, an ultraviolet-irradiating sterilizer unit, a membrane-type filter and an ultrafiltration unit to obtain a pure water having a purity higher than that of the primary pure water but lower than that of ultrapure water, passing the resulting pure water into and through a pure water feed line as connected to said ultrafiltration unit and leading to individual use point(s) of pure water, incorporating a trace amount of a water-soluble fluoride salt alone into the flow of the pure water within the pure water feed line at one or more locations of the pure water line to provide a presence of said fluoride salt at a bacteriostatic and sterilizing concentration of 0.1 to 50 ppm. in the flow of the pure water and thereby enabling the pure water to be maintained under germ-free conditions during its passage through the pure water feed line, and feeding the resulting germ-free pure water containing the trace of said fluoride salt out of the pure water feed line at the use point(s) of pure water.

3. A method for feeding germ-free pure water through a pure water feed line, which comprises providing the presence of hydrofluoric acid at a concentration of 0.1–100 ppm in a pure water to be fed, said pure water being contained in the pure water feed line, whereby the pure water is fed while being maintained under germ-free conditions with the growth of viable cells of microorganisms being suppressed by the fluoride ions present in the pure water.

4. A method for feeding germ-free pure water through a pure water feed line, which comprises providing the presence of a water-soluble fluoride salt at a concentration of 1–100 ppm in a pure water to be fed, said pure water being contained in the pure water feed line, whereby the pure water is fed while being maintained under germ-free conditions with the growth of viable cells of microorganisms being suppressed by the fluoride ions present in the pure water.

5. In the feeding of germ-free, pure water through a pure water feed line, the improvement comprising maintaining said pure water germ-free by introducing into the water, through said feed line, hydrofluoric acid at a concentration of 0.1 to 100 ppm of hydrofluoric acid and sufficient to suppress the growth of viable cells of microorganisms.

6. In the feeding of germ-free, pure water through a pure water feed line, the improvement comprising maintaining said pure water germ-free by introducing into the water, through said feed line, a water-soluble fluoride salt at a concentration of 1 to 100 ppm of said salt and sufficient to suppress growth of viable cells of microorganisms.

* * * * *